US008828074B2

(12) United States Patent
Xiao et al.

(10) Patent No.: US 8,828,074 B2
(45) Date of Patent: Sep. 9, 2014

(54) STENT GRAFT HAVING SHORT TUBE GRAFT FOR BRANCH VESSEL

(75) Inventors: Jia Hua Xiao, Santa Rosa, CA (US); Matthew Rust, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1674 days.

(21) Appl. No.: 11/379,629

(22) Filed: Apr. 21, 2006

(65) Prior Publication Data
US 2007/0250152 A1 Oct. 25, 2007

(51) Int. Cl.
*A61F 2/06* (2013.01)
*A61F 2/07* (2013.01)
*A61F 2/89* (2013.01)

(52) U.S. Cl.
CPC ............. *A61F 2/07* (2013.01); *A61F 2002/061* (2013.01); *A61F 2/89* (2013.01); *A61F 2250/006* (2013.01); *A61F 2/064* (2013.01)
USPC ........................... 623/1.13; 623/1.1; 623/1.35

(58) Field of Classification Search
CPC ...... A61F 2002/061; A61F 2/07; A61F 2/064
USPC ....................................................... 623/1.11
See application file for complete search history.

(56) References Cited

U.S. PATENT DOCUMENTS

| | | | |
|---|---|---|---|
| 4,366,819 A * | 1/1983 | Kaster ........................... 606/153 |
| 5,984,955 A | 11/1999 | Wisselink | |
| 6,168,571 B1 | 1/2001 | Solar et al. | |
| 6,395,018 B1 * | 5/2002 | Castaneda ..................... 623/1.13 |
| 6,428,565 B1 * | 8/2002 | Wisselink .................... 623/1.11 |
| 6,599,302 B2 * | 7/2003 | Houser et al. ................. 606/153 |
| 7,425,219 B2 * | 9/2008 | Quadri ......................... 623/1.35 |
| 2003/0233140 A1 | 12/2003 | Hartley et al. | |
| 2004/0098079 A1 | 5/2004 | Hartley et al. | |
| 2004/0116997 A1 * | 6/2004 | Taylor et al. ................. 623/1.11 |
| 2005/0102021 A1 * | 5/2005 | Osborne ...................... 623/1.13 |
| 2005/0131517 A1 | 6/2005 | Hartley et al. | |
| 2005/0154444 A1 * | 7/2005 | Quadri ......................... 623/1.13 |
| 2006/0058864 A1 * | 3/2006 | Schaeffer et al. ............ 623/1.11 |
| 2007/0055360 A1 * | 3/2007 | Hanson et al. ............... 623/1.35 |

FOREIGN PATENT DOCUMENTS

DE  10049828  6/2001
EP  1759660  3/2007

* cited by examiner

*Primary Examiner* — Darwin Erezo
*Assistant Examiner* — Kendra Obu

(57) ABSTRACT

A stent-graft includes a short tube graft and patch located inside of a primary graft. The patch forms a smooth and reliably sealed transition between the primary graft and the short tube graft. Accordingly, the disruption to fluid, e.g., blood, flowing through the lumen of the primary graft by the short tube graft is minimal. Further, the patch supports the inner end of the short tube graft. Thus, the patch, the short tube graft and the primary graft form a stable three-dimensional structure.

20 Claims, 14 Drawing Sheets

STENT GRAFT HAVING SHORT TUBE GRAFT FOR BRANCH VESSEL

BACKGROUND OF THE INVENTION

1. Field of the Invention

The present invention relates to an intra-vascular device and method. More particularly, the present invention relates to a device for treatment of intra-vascular diseases.

2. Description of Related Art

A conventional main stent-graft typically included a radially expandable reinforcement structure, formed from a plurality of annular stent rings, and a cylindrically shaped layer of graft material defining a lumen to which the stent rings were coupled. Main stent-grafts are well known for use in tubular shaped human vascular or other body vessel.

To illustrate, endovascular aneurysmal exclusion is a method of using a main stent-graft to exclude pressurized fluid flow from the interior of an aneurysm, thereby reducing the risk of rupture of the aneurysm and the associated invasive surgical intervention.

In instances where an aneurysm's upper limit closely approached a branch artery, such as the renal arteries, or in instances where the branch vessel emanated from a stretched or enlarged portion of an aneurysm, a main stent-graft with side openings matching the locations of the adjacent branch vessels was placed in the main vessel, e.g., the aorta, to exclude an aneurysm. Further, a branch stent graft was positioned through the side opening in the wall of the main stent graft and into the branch vessel. The branch stent graft seals the aneurysm between the opening in the sidewall of the main body and the branch vessel.

The branch opening in the sidewall of the main graft is generally a single layer of fabric graft material, where the perimeter surrounding the opening is a ring, which is kept from unraveling by being secured by a flange fixed to the perimeter of the opening or other securing method known to persons skilled in the art. Creating the connection between the thin sidewall of the graft material has been addressed by using special connectors, e.g., as described in the Wisselink U.S. Pat. Nos. 6,428,565 and 5,984,955. The procedures for installing branch grafts with special features to seal the side branch openings in the sidewall of the main graft require specialized connectors and require a high degree of surgical skill to carryout correctly. Improvements in the side branch connection system would make the process of creating such side branches easier.

SUMMARY OF THE INVENTION

In accordance with one example, a stent-graft includes a short tube graft and patch located inside of a primary graft. The patch forms a smooth transition between the primary graft and the short tube graft. Accordingly, the disruption to fluid, e.g., blood, flowing through the lumen of the primary graft by the short tube graft is minimized. Further, the patch supports the inner end of the short tube graft. Thus, the patch, the short tube graft and the primary graft form a stable three-dimensional structure.

In other examples, the short tube graft and one or more patches are located outside of the primary graft, or partially inside and partially outside of the primary graft.

Embodiments are best understood by reference to the following detailed description when read in conjunction with the accompanying drawings.

BRIEF DESCRIPTION OF THE DRAWINGS

Common reference numerals are used throughout the drawings and detailed descriptions to indicate like elements.

DETAILED DESCRIPTION

Figure 5:
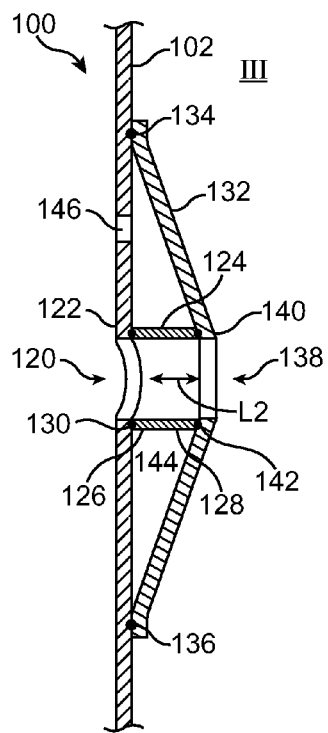
FIG. 5 is an enlarged cross-sectional view of the region V of the stent-graft of FIG. 1 and taken at V-V in FIG. 2.

In accordance with one example, referring to FIG. 5, a short tube (side branch opening) graft 124 and patch 132 are located inside of a primary graft 102. Patch 132 forms a smooth transition, sometimes called a cover, between primary graft 102 and short tube graft 124. Accordingly, the disruption to fluid, e.g., blood, flowing through lumen 111 of primary graft 102 by short tube graft 124 is minimal. Stated another way, patch 132 minimizes the turbulence created in the blood flowing through primary graft 102 due to short tube graft 124. Thus, patch 132 minimizes the restriction to blood flowing through primary graft 102.

Further, patch 132 supports inner end 128 of short tube graft 124. Thus, patch 132, short tube graft 124 and primary graft 102 form a stable three-dimensional structure.

Figure 1:
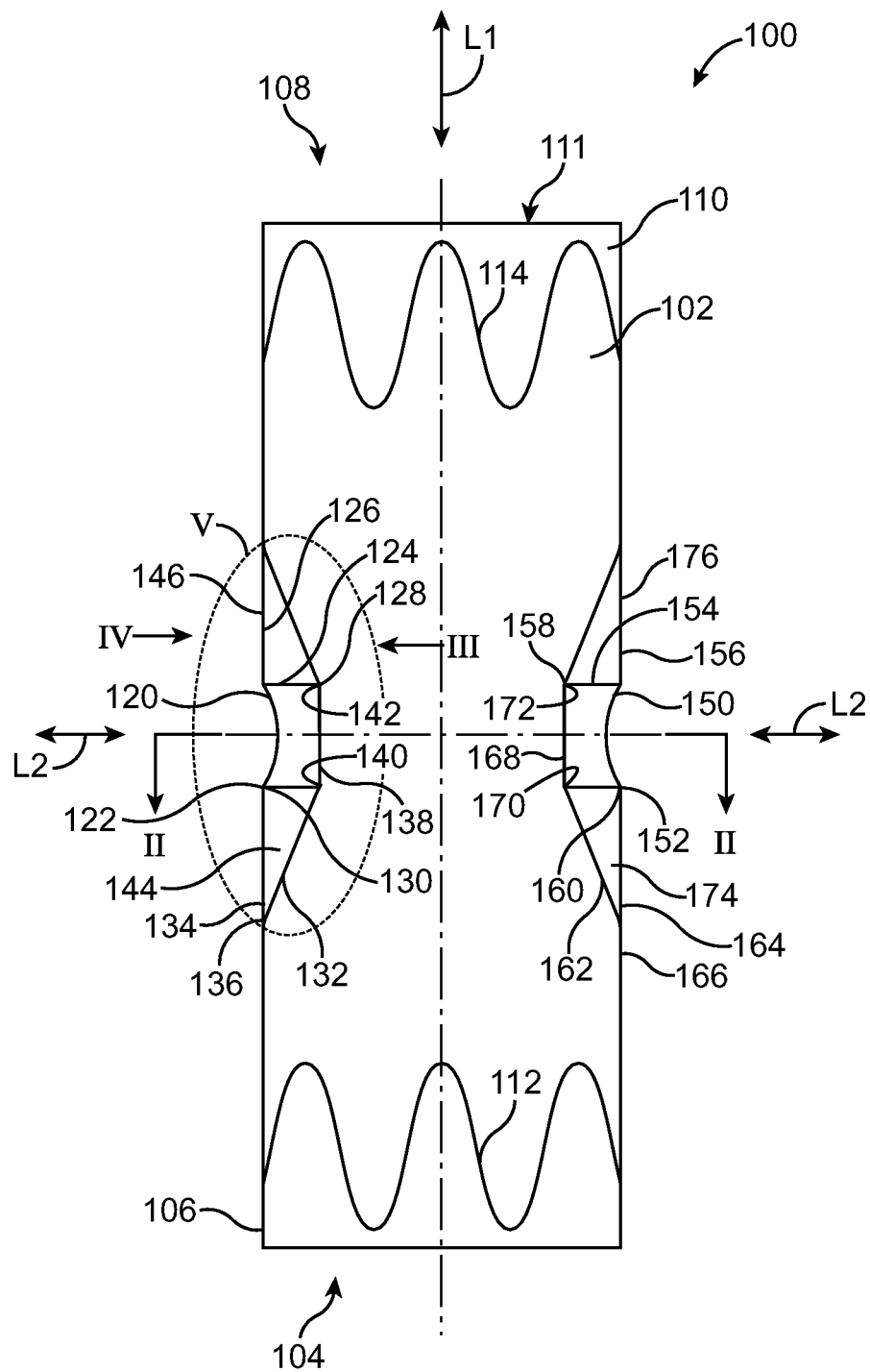
FIG. 1 is cross-sectional view of a stent-graft in accordance with one embodiment.
Figure 2:
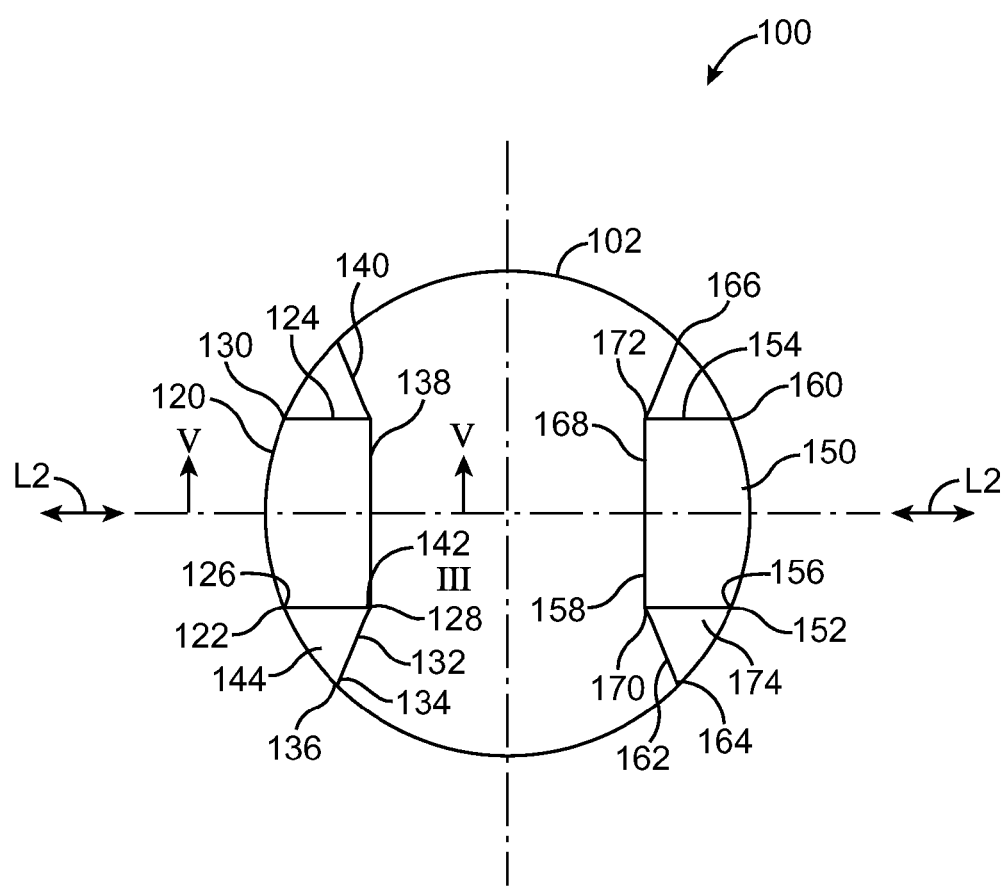
FIG. 2 is a cross-sectional view of the stent-graft taken along the line II-II of FIG. 1.

More particularly, FIG. 1 is cross-sectional view of a stent-graft 100 in accordance with one embodiment. FIG. 2 is a cross-sectional view of stent-graft 100 taken along the line II-II of FIG. 1. Referring now to FIGS. 1 and 2 together, stent-graft 100 includes a primary graft 102, e.g., a cylindrical graft material, having a longitudinal axis L1.

Primary graft 102 has a lower, e.g., first, primary opening 104 at a lower, e.g., first, end 106 of primary graft 102 and an upper, e.g., second, primary opening 108 at an upper, e.g., second, end 110 of primary graft 102. Accordingly, primary graft 102 defines a lumen 111 extending longitudinally between lower primary opening 104 and upper primary opening 108.

Stent-graft 100 further includes a lower, e.g., first, stent ring 112 at lower end 106 of primary graft 102 and an upper, e.g., second, stent ring 114 at upper end 110 of primary graft 102. In one example, stent rings 112, 114 are radially expandable reinforcement structures connected to primary graft 102 that facilitate anchoring of stent-graft 100 within a main vessel, e.g., the aorta.

Figure 3:
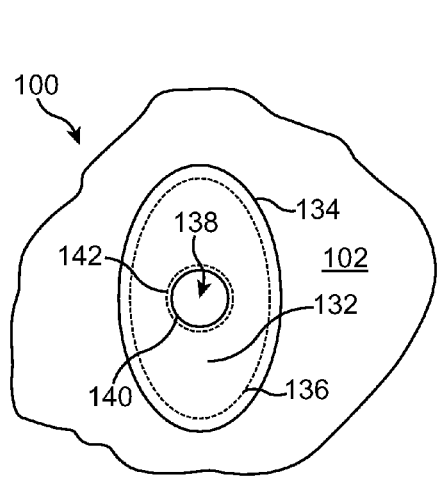
FIG. 3 is a close up partial inside view of a portion of the inside of the stent-graft as seen from the arrow III in FIG. 1.
Figure 4:
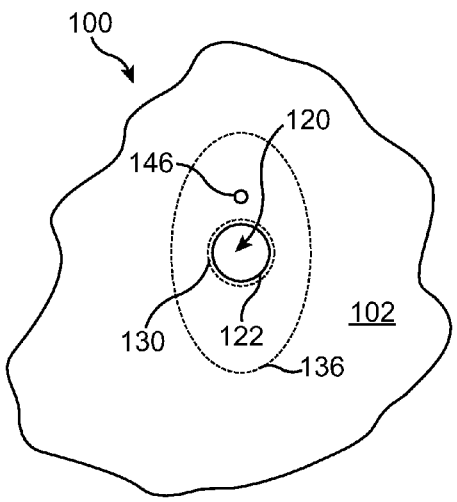
FIG. 4 is a close up partial outside view of a portion of the stent-graft as seen from arrow IV in FIG. 1.

FIG. 3 is a close up inside view of a portion of stent-graft 100 taken from the arrow III of FIG. 1. FIG. 4 is a close up outside view of a portion of stent-graft 100 taken from the arrow IV of FIG. 1. FIG. 5 is an enlarged cross-sectional view of the region V of stent-graft 100 of FIG. 1.

Referring now to FIGS. 1, 2, 4 and 5 together, formed within primary graft 102 is a first short tube opening 120. Generally, short tube opening 120 is provided in the cylindrical sidewall of primary graft 102. More particularly, short tube opening 120 is defined by a circular short tube opening edge 122 of primary graft 102.

Extending radially inward from short tube opening 120 is a first short tube graft 124, e.g., formed of a cylindrical graft material. Short tube graft 124, sometimes called a side channel, has a longitudinal axis L2 perpendicular to, sometimes called radial or lateral, to longitudinal axis L1 of primary graft 102. Short tube graft 124 includes an outer, e.g., first, end 126 and an inner, e.g., second, end 128.

Outer end 126 of short tube graft 124 is connected at short tube opening edge 122 to primary graft 102 by a short tube to primary graft bond 130. Illustratively, short tube to primary graft bond 130 is stitching, adhesive, or a thermal bond, e.g., melting, between short tube graft 124 and primary graft 102.

Referring now to FIGS. 1, 2, 3 and 5 together, inner end 128 of short tube graft 124 is connected to a patch 132. Patch 132 is oval shaped in this example, e.g., is an oval piece of graft material. However, patch 132 can be formed in other shapes, e.g., circular, rectangular, or other shape in other examples. Patch 132 includes an outer edge 134 defining an outer periphery of patch 132. Outer edge 134 is in the shape of an oval in accordance with this example.

Patch 132 is connected at outer edge 134 to primary graft 102. More particularly, outer edge 134 of patch 132 is connected to primary graft 102 around short tube opening 120 by a patch to primary graft bond 136. Illustratively, patch to primary graft bond 136 is stitching, adhesive, or a thermal bond, e.g., melting, between patch 132 and primary graft 102.

Patch 132 further includes a short tube graft opening 138 defined by a short tube graft opening edge 140 of patch 132. Short tube graft 124 extends radially outward from short tube graft opening 138. More particularly, inner end 128 of short tube graft 124 is connected at short tube graft opening edge 140 to patch 132 by a short tube graft to patch bond 142. Illustratively, short tube graft to patch bond 142 is stitching, adhesive, or a thermal bond, e.g., melting, between short tube graft 124 and patch 132.

Accordingly, primary graft 102, short tube graft 124 and patch 132 define a cavity 144. As shown in FIG. 5, a vent opening 146 is formed in primary graft 102, vent opening 146 being in fluid communication with cavity 144. Accordingly, air or fluid trapped within cavity 144 is vented through vent opening 146.

In accordance with this example, short tube graft 124 and patch 132 are located inside of primary graft 102. However, as shown in FIGS. 1, 2 and 5, patch 132 forms a smooth transition, sometimes called a cover, between primary graft 102 and short tube graft 124. Accordingly, the disruption to fluid, e.g., blood, flowing through lumen 111 of primary graft 102 by short tube graft 124 is minimal. Stated another way, patch 132 minimizes the turbulence created in the blood flowing through primary graft 102 due to short tube graft 124. Thus, patch 132 minimizes the restriction to blood flowing through primary graft 102.

Further, patch 132 supports inner end 128 of short tube graft 124. Thus, patch 132, short tube graft 124 and primary graft 102 form a stable three-dimensional structure.

Referring again to FIGS. 1 and 2 together, stent-graft 100 further includes a second short tube opening 150, a short tube opening edge 152, a short tube graft 154, an outer end 156, an inner end 158, a bond 160, a patch 162, an outer edge 164, a bond 166, a short tube graft opening 168, a short tube graft opening edge 170, a bond 172, a cavity 174, and a vent opening 176 similar to short tube opening 120, short tube opening edge 122, short tube graft 124, outer end 126, inner end 128, bond 130, patch 132, outer edge 134, bond 136, short tube graft opening 138, short tube graft opening edge 140, bond 142, cavity 144, and vent opening 146, respectively. In accordance with this example, short tube opening 150 and short tube graft 154 are substantially opposite to short tube opening 120 and short tube graft 124, although the locations are offset to match the location of the associated branch vessels.

Figure 6:
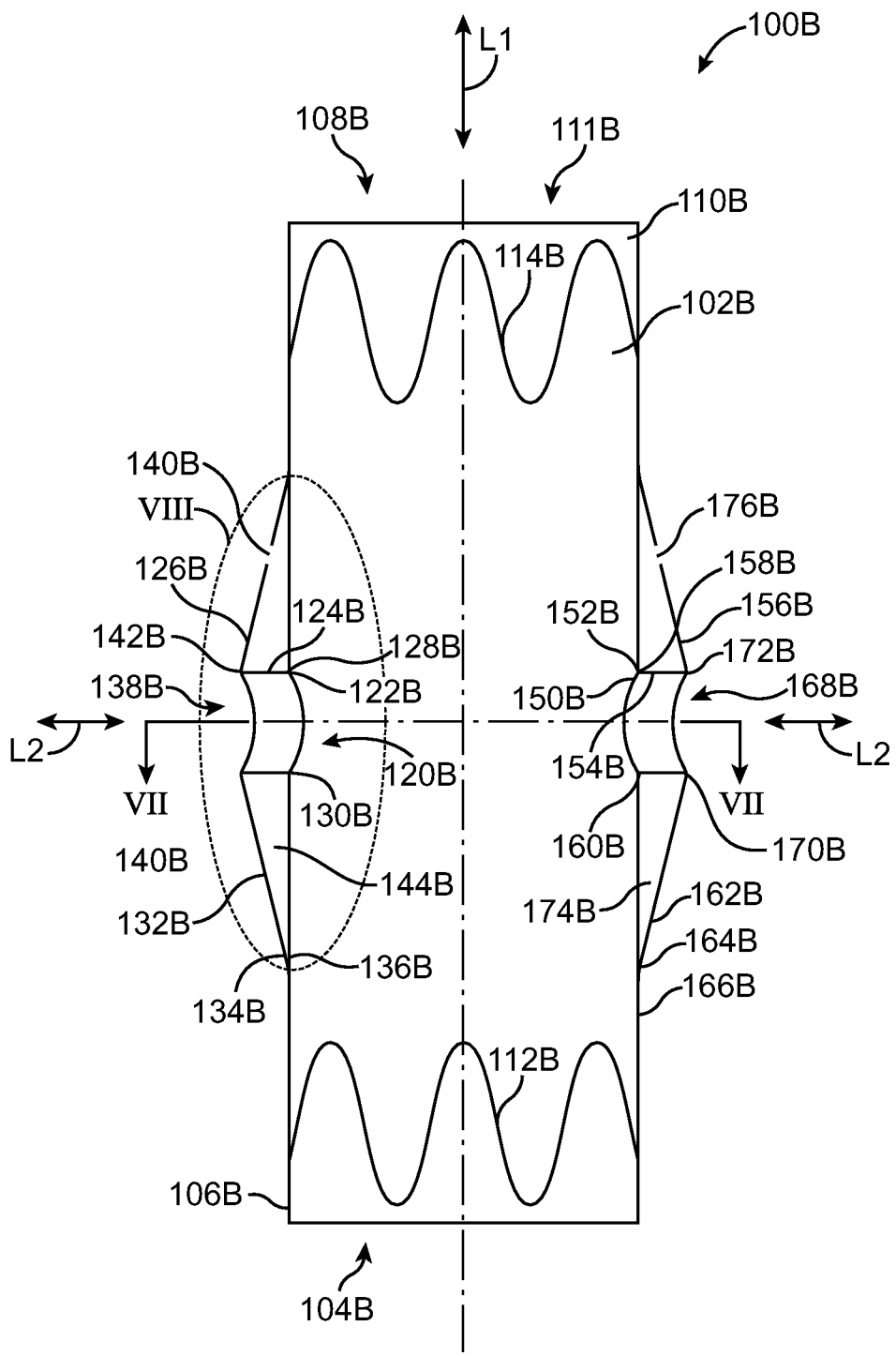
FIG. 6 is cross-sectional view of a stent-graft in accordance with one embodiment.
Figure 7:
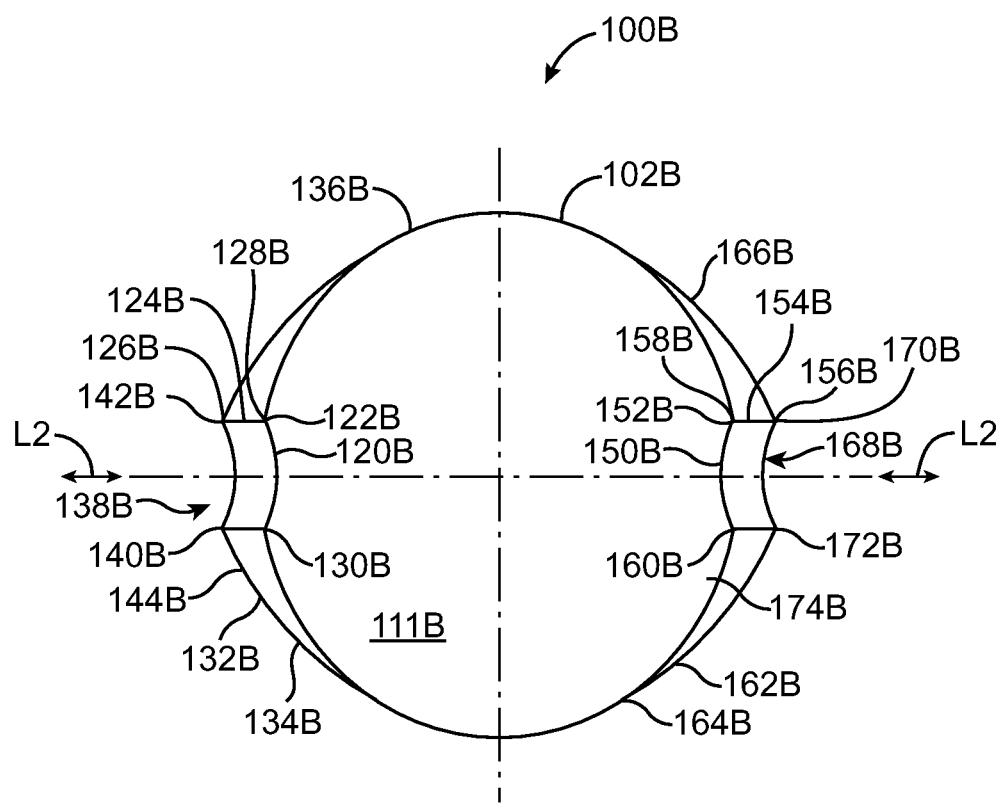
FIG. 7 is a cross-sectional view of the stent-graft taken along the line VII-VII of FIG. 6.

FIG. 6 is cross-sectional view of a stent-graft 100B in accordance with one embodiment. FIG. 7 is a cross-sectional view of stent-graft 100B taken along the line VII-VII of FIG. 6. Stent-graft 100B includes a primary graft 102B, a lower primary opening 104B, a lower end 106B, an upper primary opening 108B, an upper end 110B, a lumen 111B, a lower stent ring 112B, and an upper stent ring 114B similar to primary graft 102, lower primary opening 104, lower end 106, upper primary opening 108, upper end 110, lumen 111, lower stent ring 112, and upper stent ring 114 of stent-graft 100 of FIG. 1, respectively.

Figure 8:
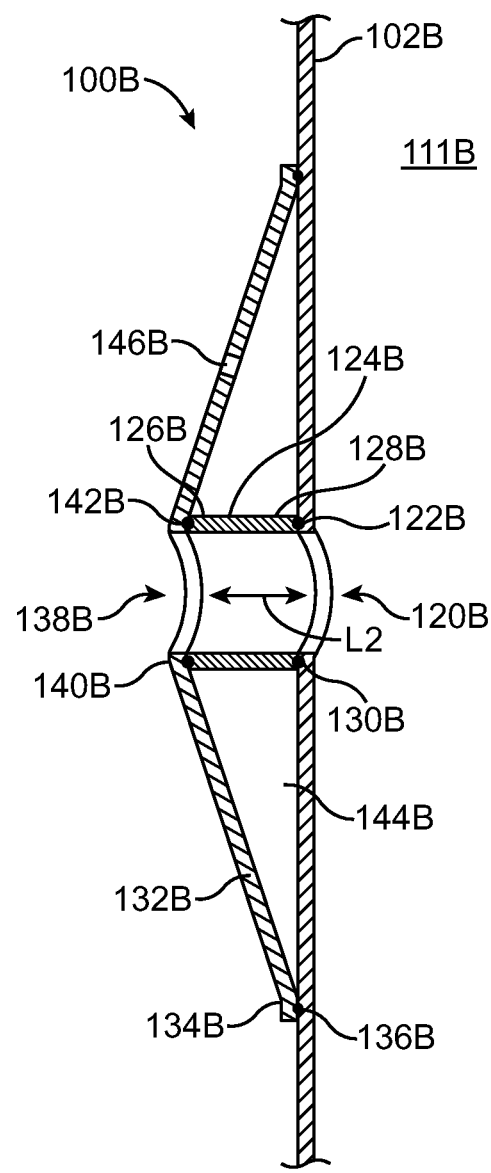
FIG. 8 is an enlarged cross-sectional view of the region VIII of the stent-graft of FIG. 6.

FIG. 8 is an enlarged cross-sectional view of the region VIII of stent-graft 100B of FIG. 6.

Referring now to FIGS. 6, 7 and 8 together, formed within primary graft 102B is a first short tube opening 120B. Generally, short tube opening 120B is formed in the cylindrical sidewall of primary graft 102B. More particularly, short tube opening 120B is defined by a circular short tube opening edge 122B of primary graft 102B.

Extending radially outward from short tube opening 120B is a first short tube graft 124B, e.g., formed of a cylindrical graft material. Short tube graft 124B has a longitudinal axis L2 perpendicular to longitudinal axis L1 of primary graft 102B. Short tube graft 124B includes an outer, e.g., first, end 126B and an inner, e.g., second, end 128B.

Inner end 128B of short tube graft 124B is connected at short tube opening edge 122B to primary graft 102B by a short tube to primary graft bond 130B. Illustratively, short tube to primary graft bond 130B is stitching, adhesive, or a thermal bond, e.g., melting, between short tube graft 124B and primary graft 102B.

Outer end 126B of short tube graft 124B is connected to a patch 132B. Patch 132B is oval shaped in this example, e.g., is an oval piece of graft material. However, patch 132B is formed in other shapes, e.g., circular, rectangular, or other shape in other examples. Patch 132B includes an outer edge 134B defining an outer periphery of patch 132B. Outer edge 134B is in the shape of an oval in accordance with this example.

Patch 132B is connected at outer edge 134B to primary graft 102B. More particularly, outer edge 134B of patch 132B is connected to primary graft 102B around short tube opening 120B by a patch to primary graft bond 136B. Illustratively, patch to primary graft bond 136B is stitching, adhesive, or a thermal bond, e.g., melting, between patch 132B and primary graft 102B.

Patch 132B further includes a short tube graft opening 138B defined by a short tube graft opening edge 140B of patch 132B. Short tube graft 124B extends radially inward from short tube graft opening 138B. More particularly, outer end 126B of short tube graft 124B is connected at short tube graft opening edge 140B to patch 132B by a short tube graft to patch bond 142B. Illustratively, short tube graft to patch bond 142B is stitching, adhesive, or a thermal bond, e.g., melting, between short tube graft 124B and patch 132B.

Accordingly, primary graft 102B, short tube graft 124B and patch 132B define a cavity 144B. As shown in FIG. 8, a vent opening 146B is formed in patch 132B, vent opening 146B being in fluid communication with cavity 144B. Accordingly, air or fluid trapped within cavity 144B is vented through vent opening 146B.

In accordance with this example, short tube graft 124B and patch 132B are located outside (the normal geometric outline of what would constitute a cylindrical tubular graft) of primary graft 102B. By locating short tube graft 124B outside of primary graft 102B, the disruption to fluid, e.g., blood, flowing through lumen 111B of primary graft 102B is minimal. Further, patch 132B support outer end 126B of short tube graft 124B forming a stable three-dimensional structure.

Referring again to FIGS. 6 and 7 together, stent-graft 100B further includes a second short tube opening 150B, a short tube opening edge 152B, a short tube graft 154B, an outer end 156B, an inner end 158B, a bond 160B, a patch 162B, an outer edge 164B, a bond 166B, a short tube graft opening 168B, a short tube graft opening edge 170B, a bond 172B, a cavity 174B and a vent opening 176B similar to short tube opening 120B, short tube opening edge 122B, short tube graft 124B, outer end 126B, inner end 128B, bond 130B, patch 132B, outer edge 134B, bond 136B, short tube graft opening 138B, short tube graft opening edge 140B, bond 142B, cavity 144B, and vent opening 146B, respectively. In accordance with this example, short tube opening 150B and short tube graft 154B are substantially opposite to short tube opening 120B and short tube graft 124B, although can be offset depending upon the location of the associated branch vessels.

Figure 9:
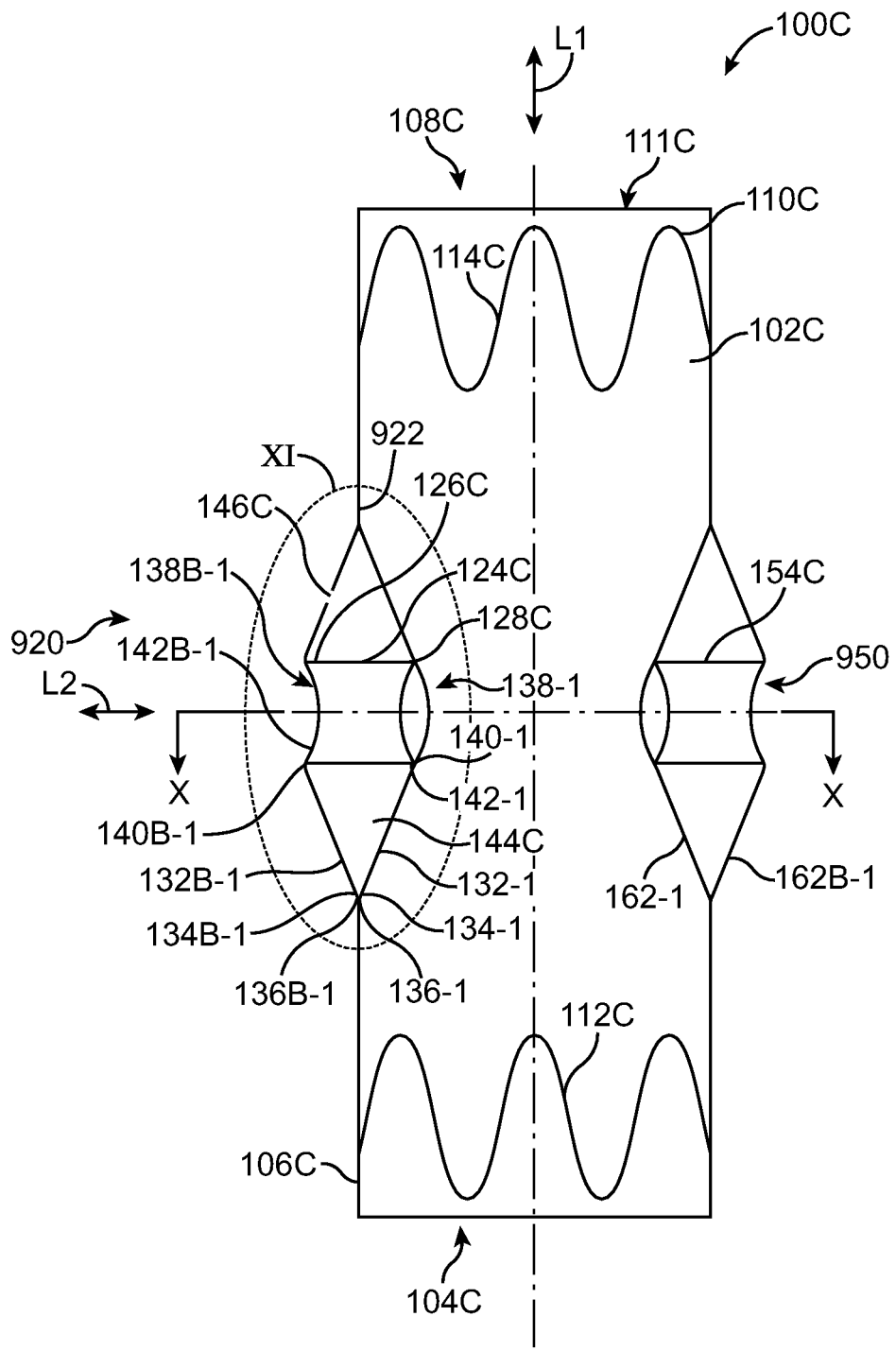
FIG. 9 is cross-sectional view of a stent-graft in accordance with one embodiment.
Figure 10:
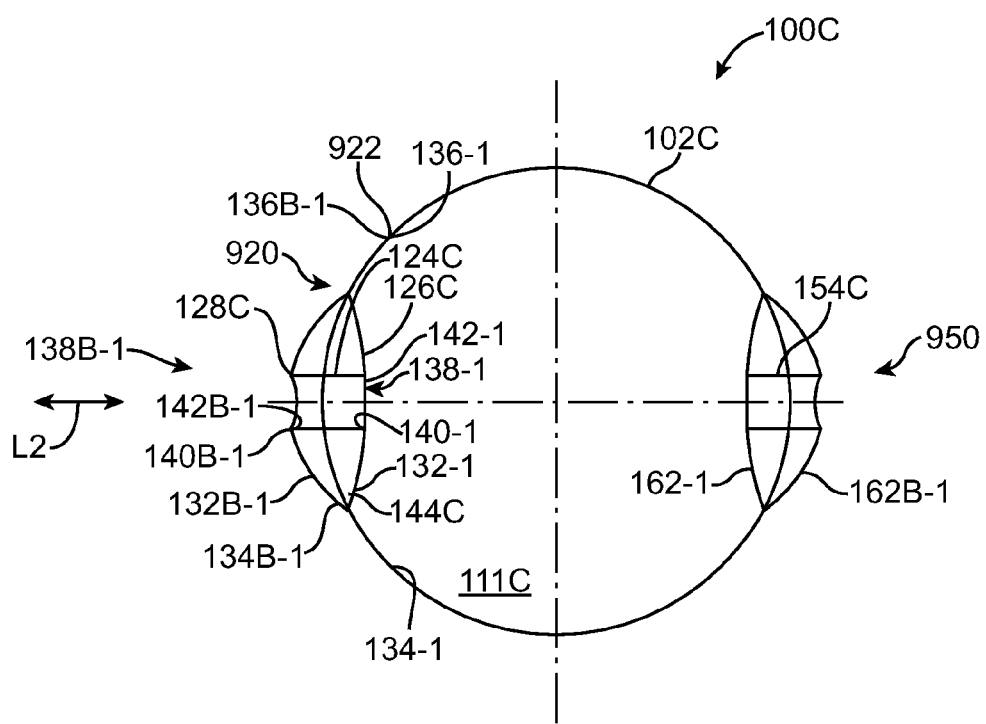
FIG. 10 is a cross-sectional view of the stent-graft taken along the line X-X of FIG. 9.

FIG. 9 is cross-sectional view of a stent-graft 100C in accordance with one embodiment. FIG. 10 is a cross-sectional view of stent-graft 100C taken along the line X-X of FIG. 9. Stent-graft 100C includes a primary graft 102C, a lower primary opening 104C, a lower end 106C, an upper primary opening 108C, an upper end 110C, a lumen 111C, a lower stent ring 112C, and an upper stent ring 114C similar to primary graft 102, lower primary opening 104, lower end 106, upper primary opening 108, upper end 110, lumen 111, lower stent ring 112, and upper stent ring 114 of stent-graft 100 of FIG. 1, respectively.

Figure 11:
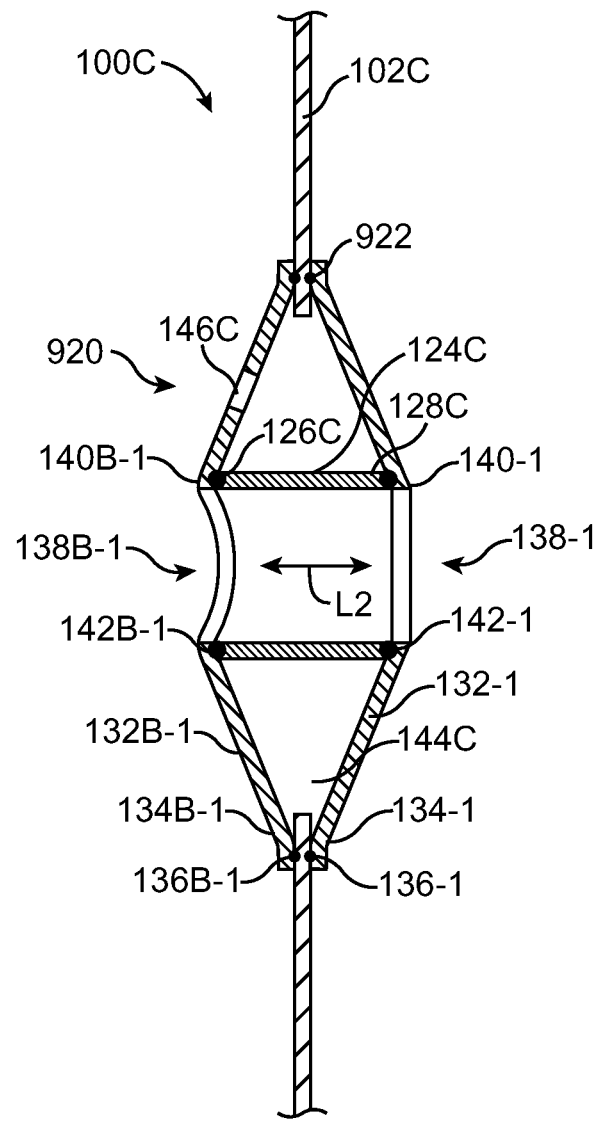
FIG. 11 is an enlarged cross-sectional view of the region XI of the stent-graft of FIG. 9.

FIG. 11 is an enlarged cross-sectional view of the region XI of stent-graft 100C of FIG. 9.

Referring now to FIGS. 9, 10 and 11 together, formed within primary graft 102C is a first short tube opening 920. Generally, short tube opening 920 is formed in the cylindrical sidewall of primary graft 102C. More particularly, short tube opening 920 is defined by a short tube opening edge 922 of primary graft 102C.

An outer patch 132B-1 is connected to primary graft 102C. Outer patch 132B-1 is oval shaped in this example, e.g., is an oval piece of graft material. However, outer patch 132B-1 is formed in other shapes, e.g., circular, rectangular, or other shape in other examples. Outer patch 132B-1 includes an outer edge 134B-1 defining an outer periphery of outer patch 132B-1. Outer edge 134B-1 is in the shape of an oval in accordance with this example.

Outer patch 132B-1 is connected at outer edge 134B-1 to primary graft 102C. More particularly, outer edge 134B-1 of outer patch 132B-1 is connected to primary graft 102C around short tube opening 920 by an outer patch to primary graft bond 136B-1. Illustratively, outer patch to primary graft bond 136B-1 is stitching, adhesive, or a thermal bond, e.g., melting, between outer patch 132B-1 and primary graft 102C.

Outer patch 132B-1 further includes a short tube graft opening 138B-1 defined by a short tube graft opening edge 140B-1 of outer patch 132B-1. A short tube graft 124C extends radially inward from short tube graft opening 138B-1. Short tube graft 124C has a longitudinal axis L2 perpendicular to longitudinal axis L1 of primary graft 102C.

Outer end 126C of short tube graft 124C is connected at short tube graft opening edge 140B-1 of outer patch 132B-1 by a short tube graft to outer patch bond 142B-1. Illustratively, short tube graft to outer patch bond 142B-1 is stitching, adhesive, or a thermal bond, e.g., melting, between short tube graft 124C and outer patch 132B-1.

An inner patch 132-1 is connected to primary graft 102C. Inner patch 132-1 is oval shaped in this example, e.g., is an oval piece of graft material. However, inner patch 132-1 is formed in other shapes, e.g., circular, rectangular, or other shape in other examples. Inner patch 132-1 includes an outer edge 134-1 defining an outer periphery of inner patch 132-1. Outer edge 134-1 is in the shape of an oval in accordance with this example.

Inner patch 132-1 is connected at outer edge 134-1 to primary graft 102C. More particularly, outer edge 134-1 of inner patch 132-1 is connected to primary graft 102C around short tube opening 920 by an inner patch to primary graft bond 136-1. Illustratively, inner patch to primary graft bond 136-1 is stitching, adhesive, or a thermal bond, e.g., melting, between inner patch 132-1 and primary graft 102C.

Inner patch 132-1 further includes a short tube graft opening 138-1 defined by a short tube graft opening edge 140-1 of inner patch 132-1. Short tube graft 124C extends radially outward from short tube graft opening 138-1. More particularly, an inner end 128C of short tube graft 124C is connected at short tube graft opening edge 140-1 to inner patch 132-1 by a short tube graft to inner patch bond 142-1. Illustratively, short tube graft to inner patch bond 142-1 is stitching, adhesive, or a thermal bond, e.g., melting, between short tube graft 124C and inner patch 132-1.

Accordingly, short tube graft 124C, inner patch 132-1, and outer patch 132B-1 define a cavity 144C. As shown in FIG. 11, a vent opening 146C is formed in outer patch 132B-1, vent opening 146C being in fluid communication with cavity 144C. Accordingly, air or fluid trapped within cavity 144C is vented through vent opening 146C.

In accordance with this example, short tube graft 124C is located partially inside and partially outside of primary graft 102C. However, as shown in FIGS. 9, 10, and 11, inner patch 132-1 forms a smooth transition, sometimes called a cover, between primary graft 102C and short tube graft 124C. Accordingly, the disruption to fluid, e.g., blood, flowing through lumen 111C of primary graft 102C by short tube graft 124C is minimal. State another way, inner patch 132-1 minimizes the turbulence created in the blood flowing through primary graft 102C due to short tube graft 124C. Thus, inner patch 132-1 minimizes the restriction to blood flowing through primary graft 102C.

Further, inner patch 132-1 and outer patch 132B-1 support short tube graft 124C. Thus, inner patch 132-1, outer patch 132B-1, and short tube graft 124C form a stable three-dimensional structure.

Referring now to FIGS. 9 and 10 together, stent-graft 100C further includes a second short tube opening 950, a short tube graft 154C, an outer patch 162B-1, and an inner patch 162-1 similar to short tube opening 920, short tube graft 124C, outer patch 132B-1, and inner patch 132-1, respectively.

Although short tube grafts 124, 124B, 124C are described above and illustrated as being perpendicular to primary grafts 102, 102B, 102C, in other examples, short tube grafts 124, 124B, 124C are angled with respect to primary grafts 102, 102B, 102C, respectively. Such an example is set forth below with reference to stent-graft 100D of FIG. 12.

Figure 12:
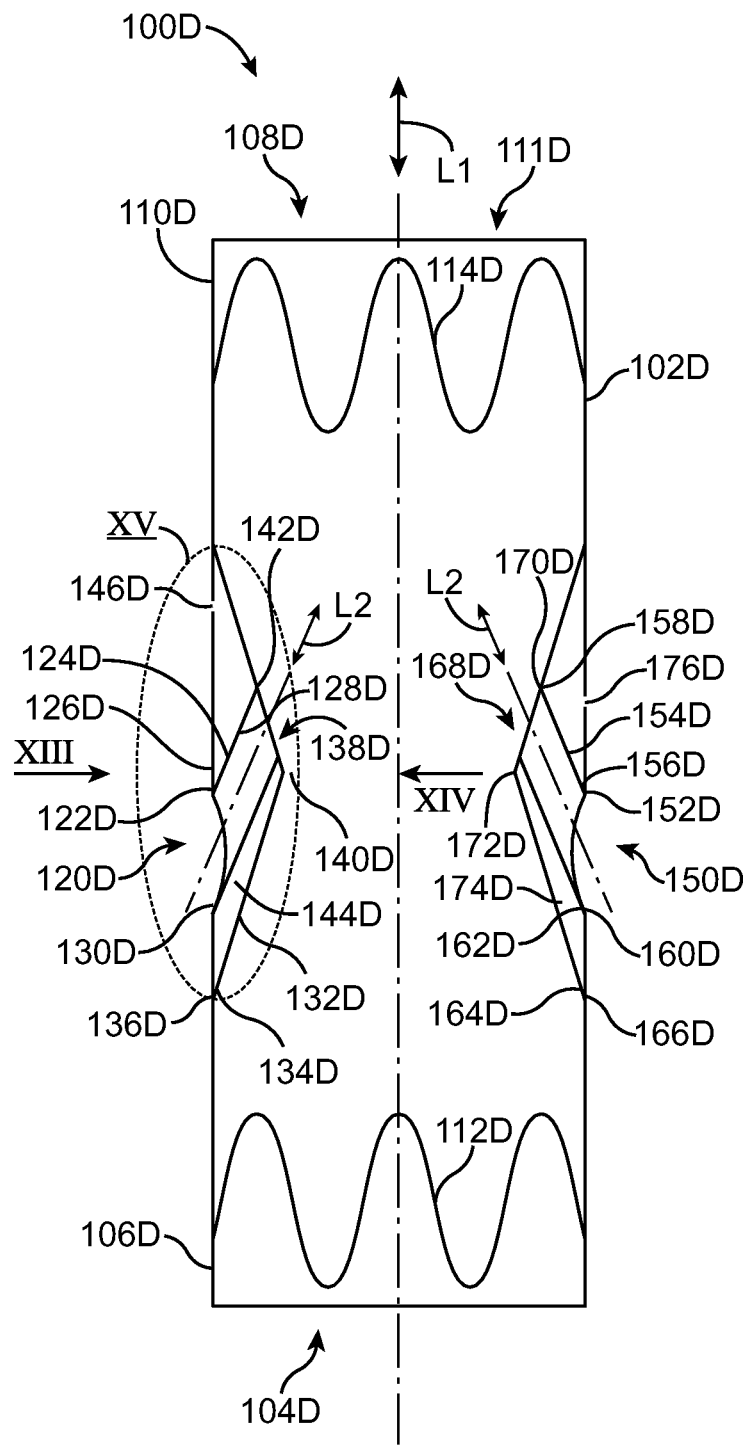
FIG. 12 is cross-sectional view of a stent-graft in accordance with one embodiment.
Figure 13:
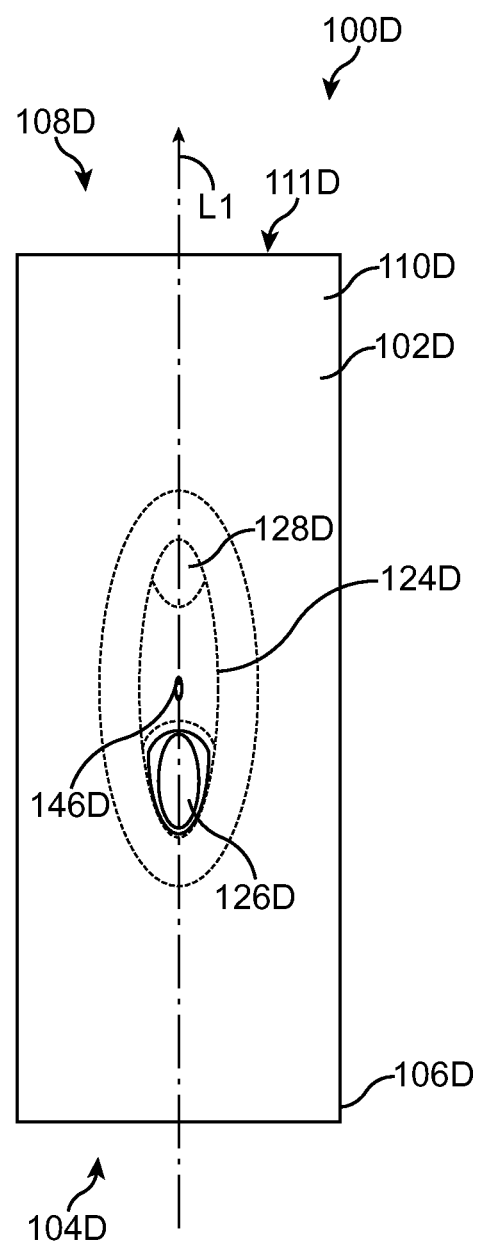
FIG. 13 is a side plan view of the outside of the stent-graft taken from the arrow XIII of FIG. 12.
Figure 14:
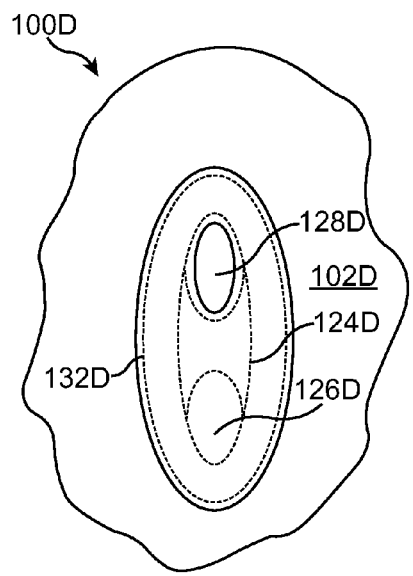
FIG. 14 is a close up inside view of a portion of the stent-graft as viewed from arrow XIV of FIG. 12.
Figure 15:
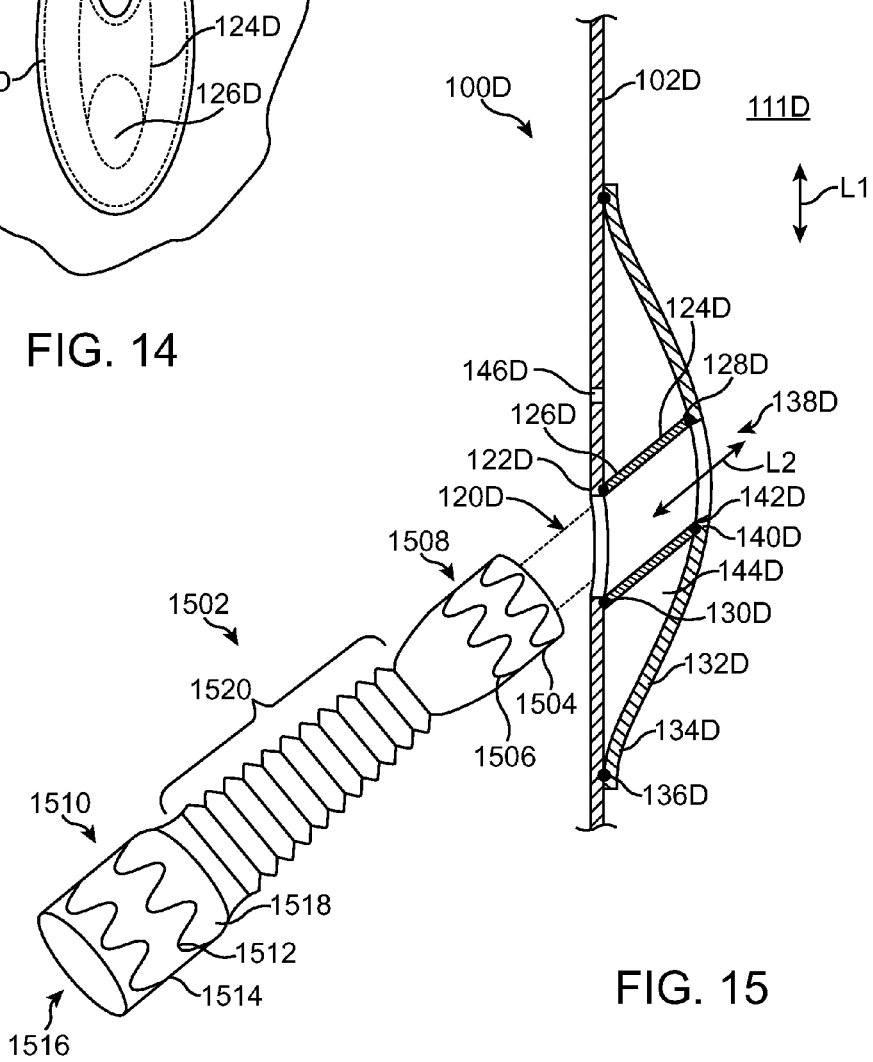
FIG. 15 is an enlarged cross-sectional view of the region XV of the stent-graft of FIG. 12.

FIG. 12 is cross-sectional view of a stent-graft 100D in accordance with one embodiment. FIG. 13 is a side plane view of stent-graft 100D taken from the arrow XIII of FIG. 12. FIG. 14 is a close up inside view of a portion of stent-graft 100D taken from the arrow XIV of FIG. 12. FIG. 15 is an enlarged cross-sectional view of the region XV of stent-graft 100D of FIG. 12.

Referring now to FIGS. 12, 13, 14 and 15 together, stent-graft 100D is substantially similar to stent-graft 100 of FIG. 1 except that stent-graft 100D is formed with short tube grafts 124D, 154D that are angled relative to primary graft 102D.

More particularly, stent-graft 100D includes a primary graft 102D, a lower primary opening 104D, a lower end 106D, an upper primary opening 108D, an upper end 110D, a lumen 111D, a lower stent ring 112D, an upper stent ring 114D, a first short tube opening 120D, a short tube opening edge 122D, short tube graft 124D, an outer end 126D, an inner end 128D, a bond 130D, a patch 132D, an outer edge 134D, a bond 136D, a short tube graft opening 138D, a short tube graft opening edge 140D, a bond 142D, a cavity 144D, a vent opening 146D, a short tube opening 150D, a short tube opening edge 152D, short tube graft 154D, an outer end 156D, an inner end 158D, a bond 160D, a patch 162D, an outer edge 164D, a bond 166D, a short tube graft opening 168D, a short tube graft opening edge 170D, a bond 172D, a cavity 174D, and a vent opening 176D similar to primary graft 102, lower primary opening 104, lower end 106, upper primary opening 108, upper end 110, lumen 111, lower stent ring 112, upper stent ring 114, first short tube opening 120, short tube opening edge 122, short tube graft 124, outer end 126, inner end 128, bond 130, patch 132, outer edge 134, bond 136, short tube graft opening 138, short tube graft opening edge 140, bond 142, cavity 144, vent opening 146, short tube opening 150, short tube opening edge 152, short tube graft 154, outer end 156, inner end 158, bond 160, patch 162, outer edge 164, bond 166, short tube graft opening 168, short tube graft opening edge 170, bond 172, cavity 174, and vent opening 176 of stent-graft 100 of FIG. 1, respectively.

However, short tube opening 120D and outer end 126D of short tube graft 124D are oval due to the angle of intersection between short tube graft 124D and the cylindrical sidewall of primary graft 102D. Further, outer end 126D of short tube graft 124D is longitudinally offset from inner end 128D of short tube graft 124D. Inner end 128D and short tube graft 124D are illustrated in the shadow line in FIG. 13 for clarity of presentation. Similarly, outer end 126D and short tube graft 124D are illustrated in the shadow line in FIG. 14 for clarity of presentation. Short tube graft 154D is substantially similar to short tube graft 124D.

By forming short tube graft 124D with a longitudinal axis L2 having an angle of intersection with longitudinal axis L1 of primary graft 102D greater than zero degrees and less than 90 degree, deployment of a branch stent-graft 1502 (see FIG. 15) into short tube graft 124D is easier compared to having to negotiate a 90 degree turn.

Referring now to FIG. 15, branch stent-graft 1502, sometimes called a renal stent-graft, is shown as a separate piece that is connected to stent-graft 100D inside of short tube graft 124D. Branch stent-graft 1502 is inserted into short tube graft 124D from the outside, e.g., through outer end 126D, of short tube graft 124D or from the inside, e.g., through inner end 128D, of short tube graft 124D.

Illustratively, stent-graft 100D is deployed within a main vessel using any one of a number of techniques well known to those of skill in the art. Illustratively, stent-graft 100D is deployed to exclude an aneurysm in the main vessel.

Short tube opening 120D is aligned with a branch vessel emanating from the main vessel. Branch stent-graft 1502, in a radially compressed state, is inserted through short tube graft 124D and into the branch vessel. For example, branch stent-graft 1502 is constrained within a sheath of a delivery catheter. Branch stent-graft 1502 is returned to its relaxed shape, e.g., to a larger diameter cylindrical shape, for example, by retracting the sheath of the delivery catheter. Illustratively, branch stent-graft 1502 includes self-expanding stent rings 1504, 1506, which are positioned inside and self-expand into short tube graft 124D thus securing branch stent-graft 1502 within short tube graft 124D and generally to stent-graft 100D.

Branch stent-graft 1502 includes an inner, e.g., first, end 1508 having stent rings 1504, 1506. As discussed above, inner end 1508 is located within short tube graft 124D and easily seals against an inner wall thereof when deployed. The precision need for branch graft placement is also reduced by the variability in seal location provided by the lateral length of the short tube graft.

An outer, e.g., second, end 1510 is deployed inside of the branch vessel. Illustratively, branch stent-graft 1502 includes self-expanding stent rings 1512, 1514, which are positioned inside and self-expand into the branch vessel thus securing branch stent-graft 1502 within the branch vessel. In one example, branch stent-graft 1502 maintains patency of the branch vessel.

Once branch stent-graft 1502 is deployed, fluid, e.g., blood, passes through a lumen 1516 of branch stent-graft 1502, e.g., from lumen 111D defined by primary graft 102D into the branch vessel. More particularly, lumen 1516 of branch stent-graft 1502 is in fluid communication with lumen 111D of primary graft 102D. Stent-graft 100D and branch stent-graft 1502 collectively form an intra-vascular assembly.

Branch stent-graft 1502 further includes a corrugated graft 1518. More particularly, corrugated graft 1518 includes a corrugated middle section 1520. Corrugated middle section 1520 accommodates variations in the characteristics, e.g., angles and locations, of branch vessels from patient to patient.

As set forth further below in reference to the modular bifurcated stent-graft assembly of FIG. 16, although only a single branch stent-graft 1502 is discussed above, in one example, a second branch stent-graft similar to branch stent-graft 1502 is mounted within short tube graft 154D in a similar manner to that discussed above.

Figure 16:
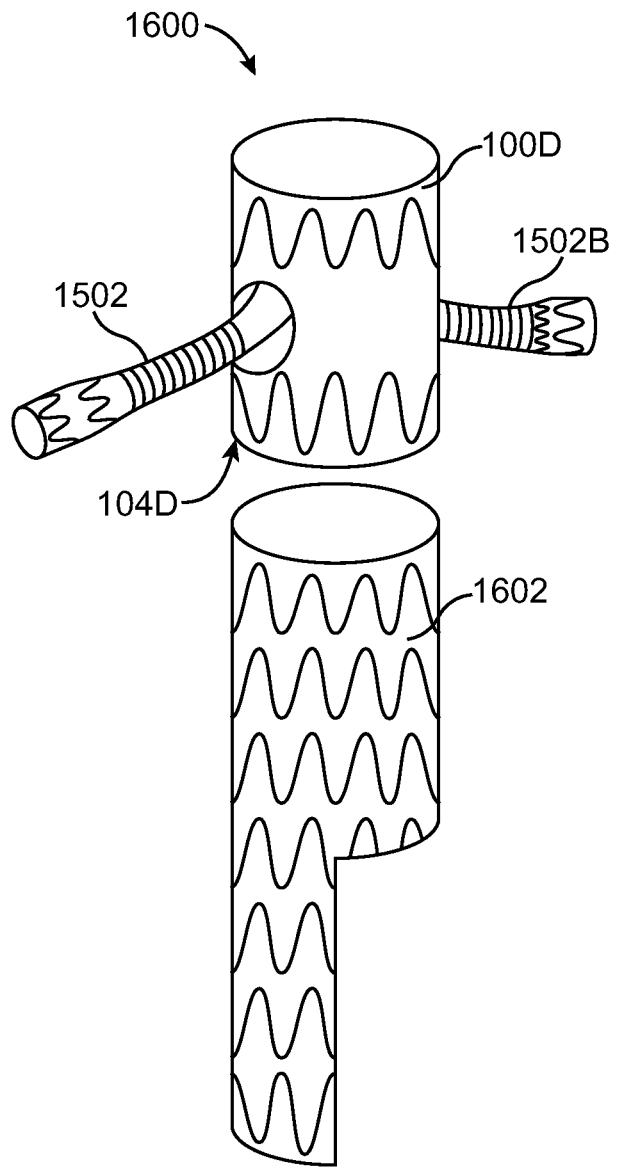
FIG. 16 is a perspective view of a modular bifurcated stent-graft assembly fabricated with the stent-graft of FIG. 12.

FIG. 16 is a perspective view of a modular bifurcated stent-graft assembly 1600 fabricated with stent-graft 100D of FIG. 12. Modular bifurcated stent-graft assembly 1600 further includes branch stent-graft 1502 of FIG. 15, a second branch stent-graft 1502B similar to branch stent-graft 1502, and a bifurcated stent-graft 1602, e.g., an iliac bifurcation. Bifurcated stent-graft 1602 is inserted into lower primary opening 104D of stent-graft 100D or vice versa.

Figure 17:
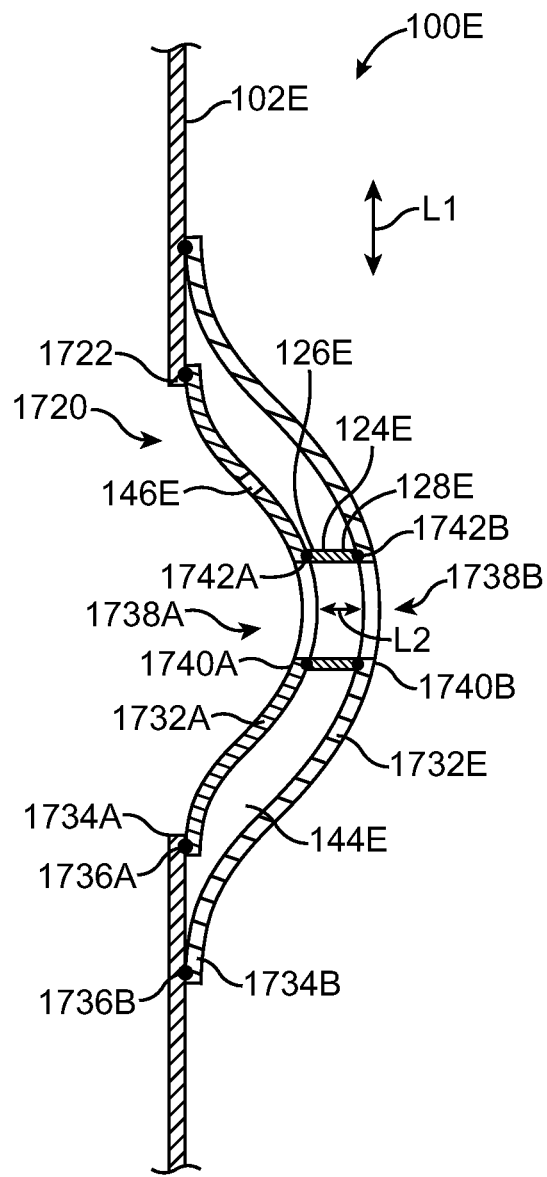
FIG. 17 is an enlarged cross-sectional view of a region of a stent-graft in accordance with another embodiment.

FIG. 17 is an enlarged cross-sectional view of a region of a stent-graft 100E in accordance with another embodiment.

Referring now to FIG. 17, formed within a primary graft 102E is a short tube opening 1720. Generally, short tube opening 1720 is formed in the cylindrical sidewall of primary graft 102E. More particularly, short tube opening 1720 is defined by a short tube opening edge 1722 of primary graft 102E.

A first inner patch 1732A, e.g., a piece of graft material, is connected to primary graft 102E. Inner patch 1732A includes an outer edge 1734A defining an outer periphery of inner patch 1732A.

Inner patch 1732A is connected at outer edge 1734A to primary graft 102E. More particularly, outer edge 1734A of inner patch 1732A is connected to primary graft 102E around short tube opening 1720 by an inner patch to primary graft bond 1736A. Illustratively, inner patch to primary graft bond 1736A is stitching, adhesive, or a thermal bond, e.g., melting, between inner patch 1732A and primary graft 102E.

Inner patch 1732A further includes a short tube graft opening 1738A defined by a short tube graft opening edge 1740A of inner patch 1732A. A short tube graft 124E extends radially inward from short tube graft opening 1738A. Short tube graft 124E has a longitudinal axis L2 perpendicular to longitudinal axis L1 of primary graft 102E.

Outer end 126E of short tube graft 124E is connected at short tube graft opening edge 1740A of inner patch 1732A by a short tube graft to patch bond 1742A. Illustratively, short tube graft to patch bond 1742A is stitching, adhesive, or a thermal bond, e.g., melting, between short tube graft 124E and inner patch 1732A.

A larger second inner patch 1732B, e.g., a piece of graft material, is also connected to primary graft 102E. Inner patch 1732B includes an outer edge 1734B defining an outer periphery of inner patch 1732B.

Inner patch 1732B is connected at outer edge 1734B to primary graft 102E. More particularly, outer edge 1734B of inner patch 1732B is connected to primary graft 102E around both short tube opening 1720 and inner patch 1732A by an inner patch to primary graft bond 1736B. Illustratively, inner patch to primary graft bond 1736B is stitching, adhesive, or a thermal bond, e.g., melting, between inner patch 1732B and primary graft 102E.

Inner patch 1732B further includes a short tube graft opening 1738B defined by a short tube graft opening edge 1740B of inner patch 1732B. Short tube graft 124E extends radially outward from short tube graft opening 1738B. More particularly, inner end 128E of short tube graft 124E is connected at short tube graft opening edge 1740B to inner patch 1732B by a short tube graft to inner patch bond 1742B. Illustratively, short tube graft to inner patch bond 1742B is stitching, adhesive, or a thermal bond, e.g., melting, between short tube graft 124E and patch 1732B.

Accordingly, primary graft 102E, inner patch 1732A, inner patch 1732B, and short tube graft 124E define a cavity 144E. As shown in FIG. 17, a vent opening 146E is formed in inner patch 1732A, vent opening 146E being in fluid communication with cavity 144E. Accordingly, air or fluid trapped within cavity 144E is vented through vent opening 146E.

By using a first inner patch 1732A and a second larger inner patch 1732B, a greater tolerance in the positioning of a branch vessel with respect to stent-graft 100E is provided. Specifically, instead of requiring the branch vessel to be aligned with outer end 126E of short tube graft 124E, the branch vessel simply needs to be aligned with short tube opening 1720 of primary graft 102E. Since short tube opening 1720 has a larger diameter than outer end 126E of short tube graft 124E, there is a greater area with which the branch vessel can be aligned.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A stent-graft assembly comprising:
   a primary graft having an outer surface and an inner surface, the inner surface defining a primary graft lumen, the primary graft including a primary graft short tube opening formed through a sidewall thereof, said primary graft short tube opening being defined by a primary graft short tube opening edge;
   a patch including an outer edge and a patch short tube opening, said patch short tube opening being defined by a patch short tube graft opening edge;
   a short tube graft extending from said primary graft short tube opening to said patch short tube opening, wherein said short tube graft includes a short tube graft inner surface defining a short tube graft lumen in fluid communication with said primary graft lumen, wherein said short tube graft forms a generally tubular wall bounded by a first end attached to and terminating at said primary graft short tube opening edge and a second end attached to and terminating at said patch short tube opening edge;
   a patch-to-primary graft bond connecting said outer edge of said patch to one of said outer surface and inner surface of said primary graft; and
   a cavity defined by one of said outer surface and inner surface of said primary graft, a surface of said patch facing said one of said outer surface and inner surface said primary graft, and an outer surface of said short tube graft between the first end and the second end of said short tube graft.

2. The stent-graft assembly of claim 1, wherein said patch-to-primary graft bond connects said outer edge of said patch to said inner surface of said primary graft, said short tube graft extends from said first end attached to said primary graft short tube opening edge radially inward towards said primary graft lumen, and said patch is disposed inside of said primary graft.

3. The stent-graft assembly of claim 2, further comprising a vent opening extending through said primary graft between said patch-to-primary graft bond and said outer surface of said short tube graft.

4. The stent-graft assembly of claim 1, wherein said patch-to-primary graft bond connects said outer edge of said patch to said outer surface of said primary graft, said short tube graft extends from said first end attached to said primary graft short tube opening edge radially outwards away from said primary graft lumen, and said patch is disposed outside of said primary graft.

5. The stent-graft assembly of claim 4, further comprising a vent opening extending through said patch between said patch-to-primary graft bond and said outer surface of said short tube graft.

6. The stent-graft assembly of claim 1, wherein said first end of said short tube graft is attached to said primary graft short tube opening edge by stitching, adhesive, or thermal bonding and said second end of said short tube graft is attached to said patch short tube opening edge by stitching, adhesive, or thermal bonding.

7. The stent-graft assembly of claim 1, further comprising:
a second primary graft short tube opening formed through a sidewall of the primary graft, said second primary graft short tube opening being defined by a second primary graft short tube opening edge;
a second patch including a second patch outer edge and a second patch short tube opening, said second patch short tube opening being defined by a second patch short tube graft opening edge;
a second short tube graft extending from said second primary graft short tube opening to said second patch short tube opening, wherein said second short tube graft includes a second short tube graft inner surface defining a second short tube graft lumen in fluid communication with said primary graft lumen, wherein said second short tube graft forms a generally tubular wall bounded by a first end attached to and terminating at said second primary graft short tube opening edge and a second end attached to and terminating at said second patch short tube opening edge;
a second patch-to-primary graft bond connecting said second outer edge of said second patch to one of said outer surface and inner surface of said primary graft; and
a second cavity defined by one of said outer surface and inner surface of said primary graft, a surface of said second patch facing said one of said outer surface and inner surface said primary graft, and an outer surface of said second short tube graft between the first end and the second end of said short tube graft.

8. The stent-graft assembly of claim 7, wherein:
said patch-to-primary graft bond connects said outer edge of said patch to said inner surface of said primary graft, said short tube graft extends from said first end attached to said primary graft short tube opening edge radially inward towards said primary graft lumen, and said patch is disposed inside of said primary graft; and
said second patch-to-primary graft bond connects said outer edge of said second patch to said inner surface of said primary graft, said second short tube graft extends from said first end attached to said second primary graft short tube opening edge radially inward towards said primary graft lumen, and said second patch is disposed inside of said primary graft.

9. The stent-graft assembly of claim 8, further comprising a second vent opening extending through said primary graft between said second patch-to-primary graft bond and said outer surface of said second short tube graft.

10. The stent-graft assembly of claim 7, wherein:
said patch-to-primary graft bond connects said outer edge of said patch to said outer surface of said primary graft, said short tube graft extends from said first end attached to said primary graft short tube opening edge radially outwards away from said primary graft lumen, and said patch is disposed outside of said primary graft; and
said second patch-to-primary graft bond connects said outer edge of said second patch to said outer surface of said primary graft, said second short tube graft extends from said first end attached to said second primary graft short tube opening edge radially outwards away said primary graft lumen, and said second patch is disposed outside of said primary graft.

11. The stent-graft assembly of claim 10, further comprising a second vent opening extending through said second patch between said second patch-to-primary graft bond and said outer surface of said second short tube graft.

12. The stent-graft assembly of claim 1, wherein a longitudinal axis of said short tube graft is generally perpendicular to a longitudinal axis of said primary graft.

13. The stent-graft assembly of claim 1, wherein a longitudinal axis of said short tube graft is angled with respect to a longitudinal axis of said primary graft such that the longitudinal axis of said short tube graft is not perpendicular to the longitudinal axis of said primary graft.

14. The stent-graft assembly of claim 1, further comprising a branch graft separate from said short tube graft and said patch, wherein an outer surface of said branch graft is in contact with said inner surface of said short tube graft.

15. The stent-graft assembly of claim 1, wherein the short tube graft and the patch are formed from graft material.

16. A stent-graft assembly comprising:
a primary graft having an outer surface and an inner surface, the inner surface defining a primary graft lumen, the primary graft including a primary graft short tube opening formed through a sidewall thereof;
a first patch including a first patch outer edge and a first patch short tube opening, said first patch short tube opening being defined by a first patch short tube graft opening edge;
a second patch including a second patch outer edge and a second patch short tube opening, said second patch short tube opening being defined by a second patch short tube graft opening edge;
a short tube graft extending from said first patch short tube opening to said second patch short tube opening, wherein said short tube graft includes a short tube graft inner surface defining a short tube graft lumen in fluid communication with said primary graft lumen, wherein said short tube graft forms a generally tubular wall bounded by a first end attached to and terminating at said first patch short tube opening edge and a second end attached to and terminating at said second patch short tube opening edge;
a first patch-to-primary graft bond connecting said first patch outer edge to one of said outer surface and inner surface of said primary graft;
a second patch-to-primary graft bond connecting said second patch outer edge to one of said outer surface and inner surface of said primary graft; and
a cavity defined said primary graft, a first surface of said first patch, a second surface of said second patch facing the first surface of said first patch, and an outer surface of said short tube graft.

17. The stent-graft assembly of claim 16, wherein said first patch-to primary graft bond connects said first patch outer edge to said outer surface of said primary graft such that said first patch is disposed outside of said primary graft and said second patch-to-primary graft bond connects said second patch outer edge to said inner surface of said primary graft such that said second patch is disposed inside of said primary graft, and wherein said short tube graft is disposed partially inside of said primary graft and partially outside of said primary graft.

18. The stent-graft assembly of claim 16, wherein said first patch-to primary graft bond connects said first patch outer edge to said inner surface of said primary graft such that said first patch is disposed inside of said primary graft and said second patch-to-primary graft bond connects said second patch outer edge to said inner surface of said primary graft such that said second patch is disposed inside of said primary graft, and wherein said short tube graft is disposed inside of said primary graft.

19. The stent-graft assembly of claim 16, further comprising a branch graft separate from said short tube graft and said first and second patches, wherein an outer surface of said branch graft is in contact with said inner surface of said short tube graft.

20. The stent-graft assembly of claim 16, wherein the short tube graft, the first patch, and the second parch are formed from graft material.

* * * * *